(12) United States Patent
Fedinec (10) Patent No.: US 8,277,417 B2
(45) Date of Patent: Oct. 2, 2012

(54) CENTRAL VENOUS CATHETER KIT WITH LINE GRIPPING AND NEEDLE LOCALIZING DEVICES

(75) Inventor: James J. Fedinec, Darien, IL (US)

(73) Assignee: James J. Fedinec, Darien, IL (US)

( * ) Notice: Subject to any disclaimer, the term of this patent is extended or adjusted under 35 U.S.C. 154(b) by 492 days.

(21) Appl. No.: 12/586,522

(22) Filed: Sep. 23, 2009

(65) Prior Publication Data

US 2011/0071394 A1   Mar. 24, 2011

(51) Int. Cl.
*A61M 5/178* (2006.01)
*A61M 25/00* (2006.01)
*A61H 1/00* (2006.01)
*A61B 5/00* (2006.01)

(52) U.S. Cl. ........ 604/164.01; 606/1; 600/585; 604/523

(58) Field of Classification Search .................. 226/127, 226/128; 600/434, 437, 439, 585; 604/116, 604/158–159; 606/108
See application file for complete search history.

(56) References Cited

U.S. PATENT DOCUMENTS

| | | | | |
|---|---|---|---|---|
| 3,745,989 A * | 7/1973 | Pinna | ............................ | 600/481 |
| 3,782,365 A * | 1/1974 | Pinna | ............................ | 600/481 |
| 3,810,459 A * | 5/1974 | Becker | ......................... | 600/453 |
| 3,998,210 A * | 12/1976 | Nosari | ......................... | 600/549 |
| 4,175,543 A * | 11/1979 | Suzuki et al. | ................. | 600/549 |
| 4,598,708 A * | 7/1986 | Beranek | ............................ | 606/1 |
| 4,615,472 A * | 10/1986 | Nash | ............................. | 226/127 |
| 4,726,369 A * | 2/1988 | Mar | ................................ | 606/1 |
| 4,829,999 A * | 5/1989 | Auth | ................................ | 606/1 |
| 4,898,178 A * | 2/1990 | Wedel | ........................... | 600/461 |
| 4,957,117 A * | 9/1990 | Wysham | ....................... | 600/585 |
| 5,131,395 A * | 7/1992 | Gehlbach | ....................... | 600/461 |
| 5,226,419 A * | 7/1993 | Hanrahan et al. | ............. | 600/437 |
| 5,235,987 A * | 8/1993 | Wolfe | ........................... | 600/461 |
| 5,243,997 A * | 9/1993 | Uflacker et al. | .............. | 600/585 |
| 5,507,300 A * | 4/1996 | Mukai et al. | ................... | 600/585 |
| 5,544,926 A * | 8/1996 | Ravencroft | .................... | 294/217 |
| 5,735,828 A * | 4/1998 | Jungnelius | ..................... | 604/264 |
| 5,758,650 A * | 6/1998 | Miller et al. | ................... | 600/461 |
| 5,897,550 A * | 4/1999 | Negus et al. | .................... | 606/10 |
| 6,132,379 A * | 10/2000 | Patacsil et al. | ................ | 600/459 |
| 6,190,333 B1 * | 2/2001 | Valencia | ........................ | 600/585 |
| 6,379,307 B1 * | 4/2002 | Filly et al. | ..................... | 600/461 |
| 6,805,669 B2 * | 10/2004 | Swanbom | ..................... | 600/437 |

(Continued)

OTHER PUBLICATIONS http://www.arrowintl.com/products/cvc/.

*Primary Examiner* — Kevin C Sirmons
*Assistant Examiner* — William Carpenter
(74) *Attorney, Agent, or Firm* — Christopher Scott (57) ABSTRACT

A central venous catheter kit enables health care workers quickly and controllably gain ultrasound supported access to vascular tissue for catheterization. Ultrasound support requires gel for reducing acoustic impedance and reflectance loss, which gel is included in the kit, as well as at least two newly conceived devices, the first for gripping the guide wire in an otherwise gelled environment, and the second for marking the skin for proper needle localization. State of the art kit components are thus included in the kit, in addition to the scanning gel and the noted device(s). The devices each comprise certain finger- or digit-grippable structure, and textured surfacing for enhancing the frictional contact between the user's digits and the devices.

11 Claims, 5 Drawing Sheets

U.S. PATENT DOCUMENTS

| | | | |
|---|---|---|---|
| 7,144,378 B2 * | 12/2006 | Arnott | 600/585 |
| 7,223,238 B2 * | 5/2007 | Swanbom | 600/437 |
| 7,241,267 B2 * | 7/2007 | Furia | 600/461 |
| 7,311,697 B2 * | 12/2007 | Osborne | 604/524 |
| 7,357,787 B2 * | 4/2008 | Moss | 604/116 |
| 7,618,430 B2 * | 11/2009 | Scheib | 606/191 |
| 7,766,839 B2 * | 8/2010 | Rogers et al. | 600/461 |
| 2003/0149366 A1 * | 8/2003 | Stringer et al. | 600/464 |
| 2004/0171988 A1 * | 9/2004 | Moretti | 604/164.01 |
| 2008/0147147 A1 * | 6/2008 | Griffiths et al. | 607/88 |
| 2009/0143760 A1 * | 6/2009 | Van Dam et al. | 604/500 |
| 2010/0041990 A1 * | 2/2010 | Schlitt et al. | 600/439 |
| 2010/0297235 A1 * | 11/2010 | Hnojewyj | 424/486 |

* cited by examiner

FIG. 1 (PRIOR ART)

FIG. 6

CENTRAL VENOUS CATHETER KIT WITH LINE GRIPPING AND NEEDLE LOCALIZING DEVICES

BACKGROUND OF THE INVENTION

1. Field of the Invention

The present invention generally relates to a central venous catheter kit, and more particularly to a central venous catheter kit usable in ultrasound supported vascular access scenarios for aiding the health care worker to expedite controlled catheterization.

2. Description of Prior Art

A central venous catheter ("central line", "CVC", "central venous line" or "central venous access catheter") is a catheter used in medicine and is typically placed into a large vein in the neck (internal jugular vein), chest (subclavian vein) or groin (femoral vein). It is typically used to administer medication or fluids, obtain blood tests (specifically the "mixed venous oxygen saturation"), and directly obtain cardiovascular measurements such as the central venous pressure. Certain medications, such as inotropes and amiodarone, are preferably given through a central line.

A central venous catheter is typically inserted by first cleaning the skin, and applying a local anesthetic if required. The location of the vein is then identified by landmarks or with the use of an ultrasound device, which device is optimally functional when used in conjunction with ultrasound scanning gel. Notably, medical sonography is an ultrasound-based diagnostic imaging technique used to externally visualize otherwise internally located muscles, tendons, and organs, including size, structure with real time tomographic images. The scanning gel is superficially applicable to a skin layer as a couplant that provides an acoustic pathway between the transducer and the skin.

A hollow needle (i.e. and insertion of introduction needle) is advanced through the skin until blood is aspirated. The Seldinger technique is then commonly used or employed to insert the line. This means that a blunt guide wire is passed through the needle, and the needle is then removed. A dilating device may be passed over the guide wire to slightly enlarge the tract, and the central line itself is then passed over the guide wire, which is then removed. All the lumens of the line may then be aspirated for the purpose of ensuring proper positioning thereof, and flushed.

In order to properly pass the guide wire through the needle, the user must be able to grip the wire so that the wire may be properly and controllably advanced. This becomes difficult in emergency scenarios when hardware-lubricating ultrasound scanning gel has been inadvertently applied to the guide wire and/or the health care worker's hands. Thus, it is conceived that certain line or wire gripping or grabbing means, usable in combination with a basic central venous catheter kit, inclusive of ultrasound scanning gel, may expedite the health care worker's ability to controllably place a medically necessary central venous catheter.

Central venous catheter kits are known. An exemplary central venous catheter kit is supplied by Arrow International, Inc., a subsidiary of Teleflex International with corporate headquarters being located at 155 South Limerick Road, Limerick, Pa., 19468-1699, United States of America. None of the known central venous catheter kits currently available include ultrasound scanning gel, line or wire gripping or grabbing means and/or needle localizing means. In emergency medicine scenarios, instantaneous availability of the proper equipment is critical to proper emergency medicine practice. Thus, the prior art perceives a need for a central venous catheter kit comprising the preferred equipment as here indicated.

SUMMARY OF THE INVENTION

It is thus an object of the current invention to provide a central venous catheter kit generally comprising a number of the following components: a gel pack or scanning gel; rubber band or ring; a transducer cover; a tissue or vessel dilator; certain needle localizing means; an introducer needle or introduction syringe (e.g. 18 gauge); an injection needle (e.g. Luer-slip syringe (e.g. 22 gauge) or Luer-lock syringe (e.g. 25 gauge)); indwelling catheter (e.g. multi-lumen); spring-wire guide or guide wire; a needle holder; Lidocaine solution; an applicator assembly; a catheter clamp; a clamp fastener; and certain line or wire gripping/grabbing means.

It is a further object of the present invention to provide a central venous catheter kit for helping a health care worker gain ultrasound-supported, vascular access, which kit more particularly comprises ultrasound scanning gel superficially applicable to a skin layer for properly coupling the skin layer and an ultrasound device; an insertion needle for accessing a vein; a guide wire, cooperable with the insertion needle for guiding structure to the accessed vein; certain wire gripping means for enhancing a health care worker's grip on the guide wire (in a lubricated environment); and a catheter, insertable into the accessed vein via the guide wire.

A summary listing of the contemplated kit contents, along with designated reference numbers, as follows:

Gel bag 10
Gel 11
Rubber band or ring 12
Transducer cover 13
Tissue dilator 14
Introducer needle or Introduction Syringe 15 (18 gauge)
Injection needle Luer-slip syringe 16 (22 gauge)
Injection needle Luer-lock syringe 17 (25 gauge)
Multi-lumen indwelling catheter 18
Spring-wire guide 19
Catheter assembly 20
Needle holder 21
Safety scalpel 22
Applicator device 23
Catheter clamp 24
Clamp fastener 25
Lidocaine solution 26
Line grabbing device 30
Needle localizing device 40

BRIEF DESCRIPTION OF THE DRAWINGS

Other features of my invention will become more evident from a consideration of the following brief description of patent drawings.

DESCRIPTION OF THE PREFERRED EMBODIMENT(s)

Figure 1:
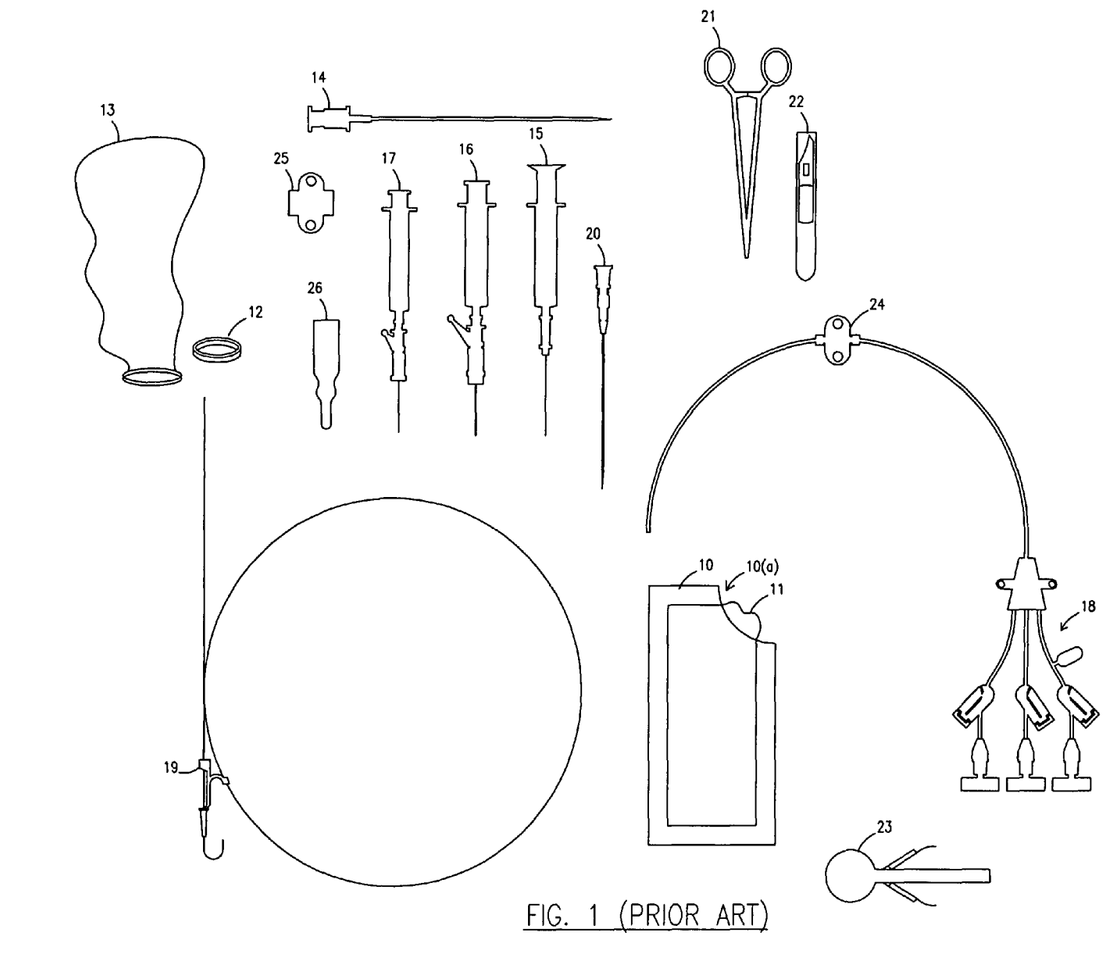
FIG. 1 is a diagrammatic type depiction of various prior art components set forth in the foregoing summary listing, including a gel bag or pack having ultrasound scanning gel, rubber band or ring, transducer cover, tissue or vessel dilator, introducer needle or introduction syringe, injection needle (e.g. Luer-slip syringe) injection needle (e.g. Luer-lock syringe); multi-lumen indwelling catheter, spring-wire guide, catheter assembly, needle holder, safety scalpel, applicator device, catheter clamp, and clamp fastener.
Figures 2, 3:
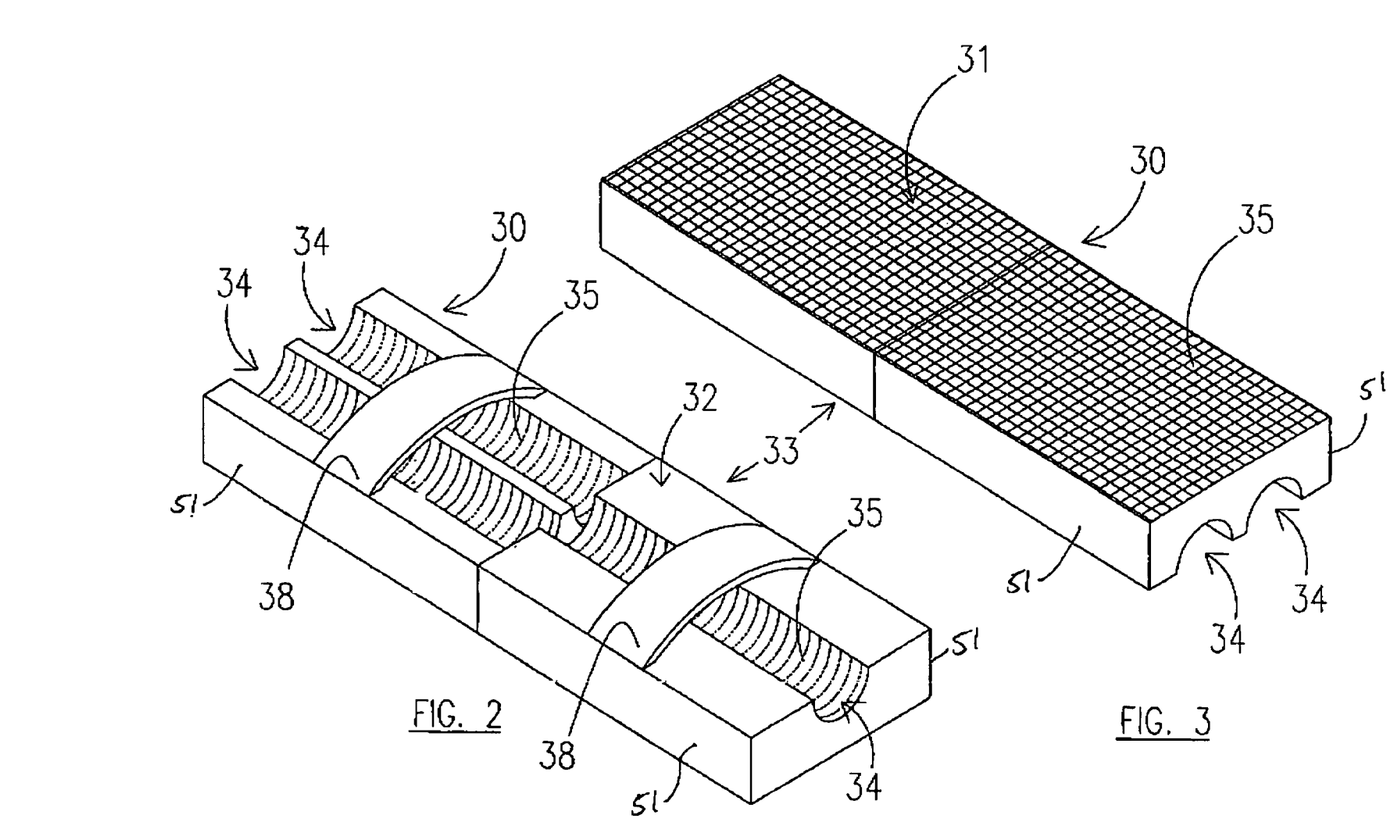
FIG. 2 is first perspective view of a line or wire gripping or grabbing device according to the present invention showing the device in an unfolded, expanded configuration with a first surface thereof.
FIG. 3 is second perspective view of the line or wire gripping or grabbing device according to the present invention showing the device in an unfolded, expanded configuration with a second surface thereof.
Figure 4:
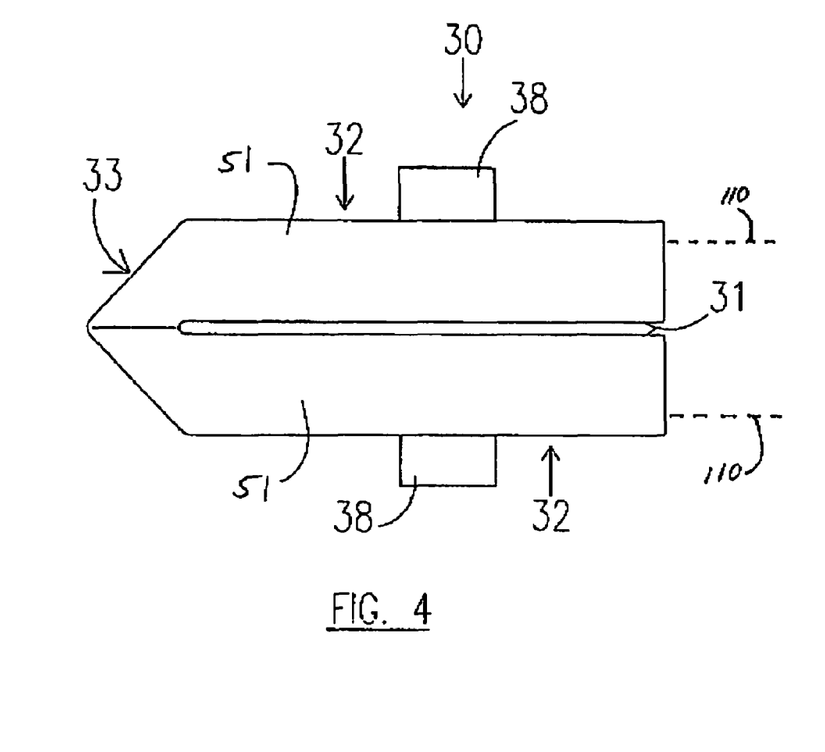
FIG. 4 is side view of the line or wire gripping or grabbing device according to the present invention showing the device in a folded configuration.
Figure 5:
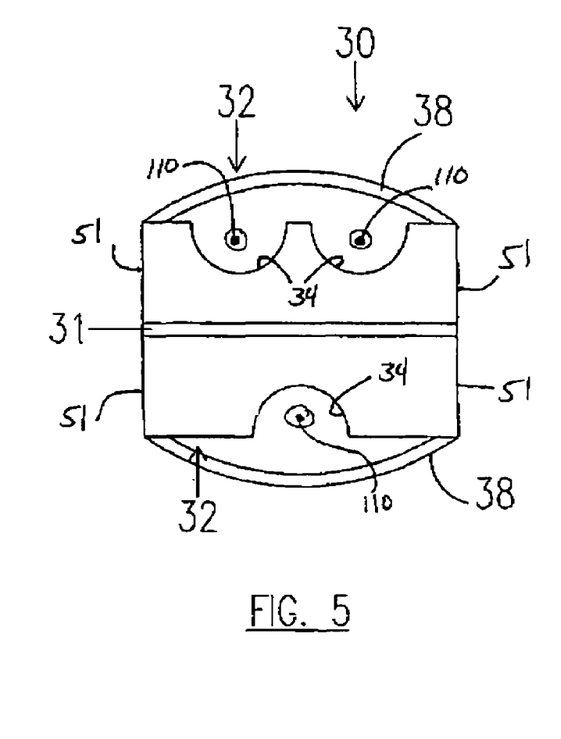
FIG. 5 is end view of the line or wire gripping or grabbing device according to the present invention showing the device in a folded configuration.
Figure 6:
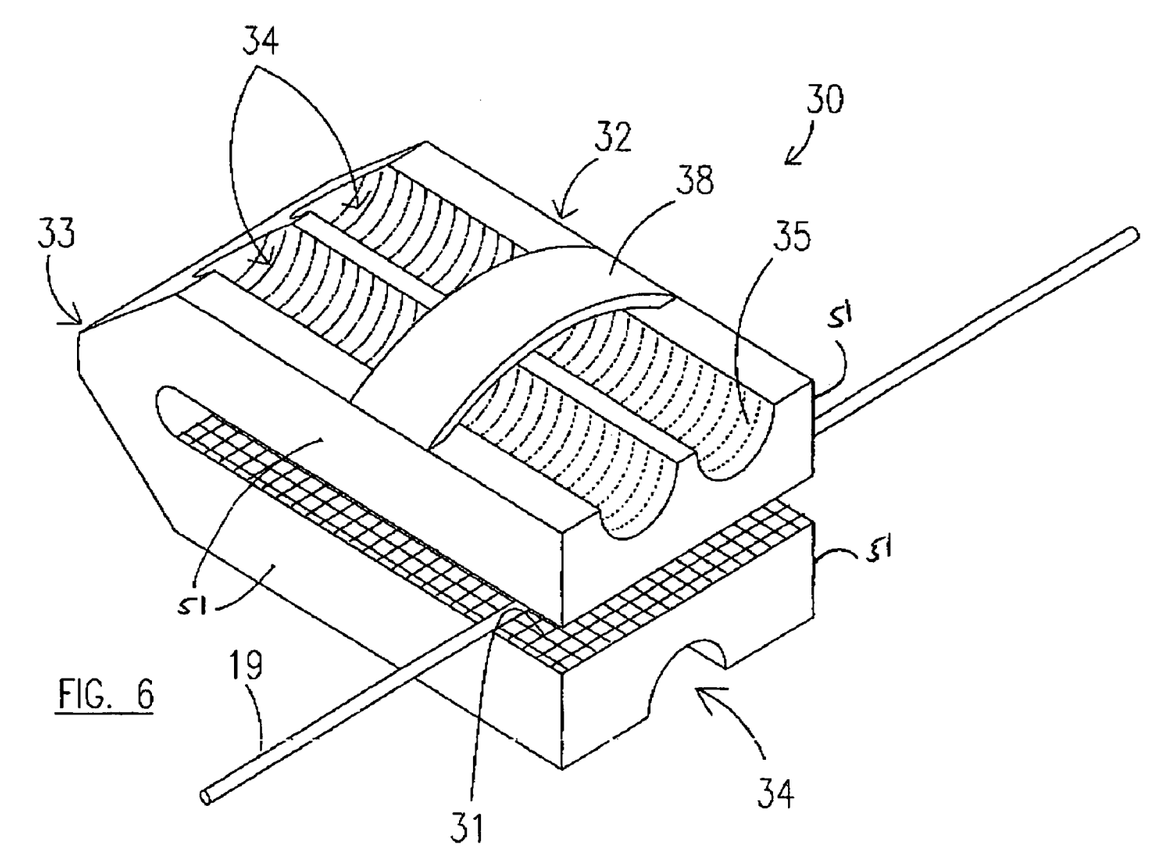
FIG. 6 is a perspective view of the line or wire gripping or grabbing device according to the present invention showing the device in a folded configuration with a fragmentary guide wire extending therethrough sandwiched between the second surface.

Referring now to the drawings with more specificity, the preferred embodiment of the present invention generally concerns a central venous catheter kit generally usable in an emergency room setting. In this regard, it has been noted that ultrasound supported vascular access for implanting a catheter is of great benefit to emergency health care workers. Ultrasound-supported vascular access, however, requires or is greatly aided by the application of ultrasound gel 11 (as provided in gel packs or gel containers as at 10). The gel pack 10 depicted in FIG. 1 is shown with a broken corner as at 10(a) to show gel 11 outlet from the corner 10(a).

Ultrasound transmission or "scanning" gels are typically found everywhere diagnostic ultrasonic imaging is performed, and are commonly used in combination with catheterization processes so as to aid the physician or catheterization technician with more accurately locating underlying vein anatomy for easing and enhancing catheterization. Because the primary purpose of the scanning gel is to eliminate any possibility of air that is caught at the transducer interface, which would result in a huge acoustic impedance mismatch that is near impossible to overcome to image structures. Thus the efficiency and accuracy of the transmission is of primary importance.

Reflection of the sound beam occurs when it hits a boundary between materials having different acoustic impedance. This reflection within the body produces the ultrasound image, but should be minimized at the couplant to skin boundary where the couplant acts as an acoustic window through which the image is seen. Just as reflections from a glass window can sometimes obscure what is on the other side, lack of a couplant match causes reflections that decrease acoustic wave transfer and makes imaging of structures near impossible.

For the purposes of this specification, it will suffice to state that ultrasound scanning gel 11 is an important element to the kit. Notably, however, the scanning gel 11 not only acts as a couplant for providing an acoustic pathway between the transducer and the skin 105, but also inadvertently tends to lubricate other hardware such as the guide wire 19, which gel 11 makes gripping contact with the guide wire 19 more difficult. Certain wire or line gripping means (as described in more detail hereinafter) are thus further contemplated to aid the health care worker or user selectively and manually grip the guide wire or line 19 so that quick and proper placement of the guide wire 19 may be achieved.

The central venous catheter kit according to the present invention is thus conceived as a means to aiding a health care worker gain ultrasound-supported, vascular access, and to achieve this essential goal, the kit may be said to comprise gel as at 11; a transducer cover as at 13; a tissue or vessel dilator as at 14; an insertion or introducer needle or syringe as at 15; one or more injection needles or syringes (e.g. 22 gauge Luer-slip type syringe as at 16 or 25 gauge Luer-lock type syringe as at 17); and a multi-lumen indwelling catheter as generally depicted at 18.

Further, the kit may be said to comprise a spring-wire guide or guide wire 19; a catheter-introducer needles assembly (as generally depicted at 20); a needle holder as at 21; a catheter clamp 24; a clamp fastener 25, a portion of Lidocaine solution 22; and an applicator device as at 23. Other kit items or elements could conceivably include a cap, a gown, a mask with splashield, a drape (68"×110" w/4" hole), gloves size 7½, styrofoam block for sharps, 0.9 Ns saline flush 20 cc, Betadine gel, Large Tegaderm, 4×4 and 2×2 gauze(s), and 3-0 Nylon suture pack for anchoring line.

Further, as noted above, the kit may be said to comprise certain wire or line grabbing or gripping means, as exemplified by a device 30 and certain needle localizing means, as exemplified by a device 40. The line or wire gripping device 30 according to the present invention is generally depicted in FIGS. 2-6. The needle localizing device 40 according to the present invention is generally depicted in FIGS. 7-10. From a general inspection of the noted figures, it will be seen that the wire gripping device 30 generally takes the form of a pad and the needle localizing device 40 generally takes the form of a stylus with an apertured tip, the latter of which is very much akin to the cone-shaped tip of the housing of a retractable pen.

Figures 7, 8, 9, 10:
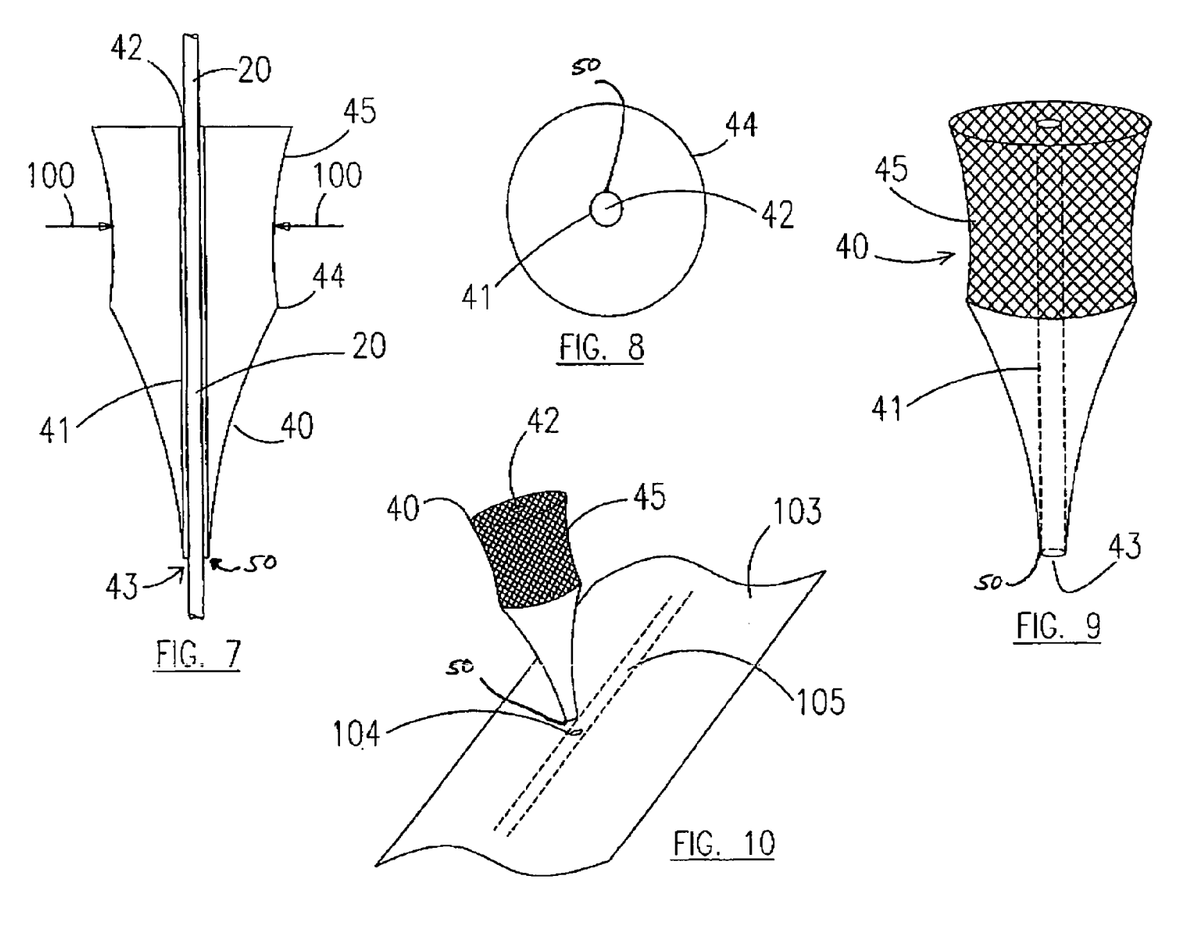
FIG. 7 is a longitudinal cross section of a needle localizing device according to the present invention showing a needle extending through a central tunnel formed therein.
FIG. 8 is a transverse cross section of the needle localizing device or needle localizer according to the present invention showing an axial view of the needle-receiving tunnel.
FIG. 9 is a top perspective view of the needle localizing device according to the present invention.
FIG. 10 is a top perspective view of the needle localizing device according to the present invention in superficial adjacency to a skin layer showing a vein (in broken lines) deep to the outer skin surface, which outer skin surface has been marked with a needle localizing circle via the needle localizing device.

The needle localizing stylus or device 40 is preferably constructed from a relatively rigid material suitable for depressing skin (as at 103 in FIG. 10) and leaving a vein localizing depression or mark as at 104 via a pointed or sharpened outer tin diameter as at 50 for marking the location of an underlying vein as at 105. The device 40 preferably comprises a circular cross section through a first or transverse plane as generally depicted in FIG. 8; a pointed cross section through a second or longitudinal plane orthogonal to the first or transverse plane as generally depicted in FIG. 7; and an optional tunnel 41 extending through the stylus or device 40 for axially receiving an insertion needle 19. The needle 19 is thus insertable through the tunnel 41 for direct insertion into a vein 105 via the stylus or device 40.

In other words, the relatively rigid material of the stylus 40 (as compared to the pliability of the skin 103) enables the health care worker to selectively and manually depress the skin 103 in superficial adjacency to the underlying vein 105 (as located via ultrasound hardware, etc.) and thereby leave a vein locating mark 104 for more accurately locating the needle 19 relative to the vein or vascular target.

It may be seen from a comparative inspection of FIG. 7 versus FIG. 8 that the circular cross section has a center as at 42 and that the pointed cross section has a tip as at 43. It is contemplated that the tunnel 41 preferably extends axially through the stylus 40 along the center 42 to the tip 43. Further, the stylus 40 is contemplated to preferably comprise an outer stylus surface as at 44, which outer stylus surface 44 comprises certain stylus gripping means for enhancing a user's grip (as at arrows 100 in FIG. 7) on the stylus 40. The stylus gripping means may be exemplified by certain textured structure 45 (for increasing effective surface area at the contact interface) as generally depicted by the cross-hatching in FIGS. 9 and 10.

The line gripping pad or device 30 is preferably constructed from a resiliently flexible or pliable material and comprises a first pad surface as at 31, a second pad surface 32 opposite the first pad surface 31, and a central or centralized fold section as generally referenced at 33. The device or pad 30 is thus foldable at the central fold section 33 for sandwiching the guide wire 19 intermediate opposing portions of the first pad surface 31 or simply with the first pad surface 31. The second pad surface 32 further preferably comprises certain pad gripping means for enhancing the health care worker' grip on the pad 30.

The guide wire 19 is thus displaceable relative to the pad 30 via the first pad surface 31. The resiliently flexible material of the pad or device 30 enables the health care worker to selectively and manually pinch-grip the guide wire 19 for more controllably locating the wire 19 relative to the vein or vascular target. The first pad surface 31 may further preferably comprise certain friction enhancing means for enhancing friction between the pad 30 and the guide wire 19 when the health care worker selectively and manually pinch-grips the wire 19. The friction enhancing means may be exemplified by certain textured structure 35 (for increasing effective surface area at the contact interface) as generally depicted by the cross-hatching in FIGS. 2, 3, and 6.

The pad gripping means of the second pad surface may preferably comprise digit receiving notches 34 as generally depicted in FIGS. 2, 3, 5, and 6. In this regard, it should be noted that pad 30 may preferably comprise a first half as at 36 and a second half as at 37. A single digit receiving notch 34 is perferably formed in the first half 36 at the second pad surface 32 intermediate the lateral edges for receiving the health care worker's thumb and at least one, but preferably two, digit receiving notch(es) 34 is/are preferably formed in the second half 37 at the second pad surface 32 in staggered relation relative to the single thumb-receiving notch 34 intermediate the lateral edges 51 for receiving at least one of the health care worker's fingers. The notches 34 preferably comprise notch axes as at 110, which notch axes extend parallel to the lateral edges 51 of the pad 30.

The notches 34 may be similarly outfitted with certain friction enhancing means (as referenced at 35) for enhancing friction between the pad 30 and the health tare worker's digits. The friction enhancing means may be exemplified by certain textured structure 35 (for increasing effective surface area at the contact interface) as generally depicted by the cross-hatching in FIGS. 2 and 6. It may be seen from an inspection of FIGS. 2 and 6 that the textured surfacing within the notches extends laterally or in an edge 51-to-edge 51 direction generally perpendicular to the axes 110 for enhancing friction between the pad 30 and the health care worker's digits.

Certain digit-retaining means as exemplified by laterally extending straps 38 (also extending in an edge 51-to-edge 51 direction across the notches 34) are further contemplated and incorporated in the line gripping device 30. In this regard, it is contemplated that when the health care workers digits or fingers are inserted into notches 34, the laterally extending straps 38 may well function to retain the user's digits within the notches 34 so that line gripping effectiveness of the device 30 is enhanced.

While the above description contains much specificity, this specificity should not be construed as limitations on the scope of the invention, but rather as an exemplification of the invention. For example, it is contemplated that the present invention essentially provides a venous catheter kit for helping a user gain controlled vascular access. The venous catheter kit according to the present invention is believed to essentially comprise needle-localizing means for marking the outer skin surface for proper needle insertion; an insertion needle for accessing a localized vein; a guide wire cooperable with the insertion needle for guiding structure to the accessed vein; certain wire gripping means for enhancing a user's grip on the guide wire; and a catheter, the catheter being insertable into the accessed vein via the guide wire.

It is contemplated that the wire gripping means may be preferably defined by a line gripping pad (as exemplified by device 30). The pad 30 is preferably constructed from a resiliently flexible or pliable material for transferring manipulative force against the line or wire 19 for gripping the same. The wire thus becomes more controllably displaceable relative to the wire gripping means, particularly in a lubricated environment, which is often the case where ultrasound hardware and ultrasound scanning gel supports the vascular access process.

It is contemplated that the needle-localizing means may be preferably defined by a needle localizing device (as exemplified by device 40). The device 40 is preferably constructed from a material relatively rigid as compared to the superficial dermis for making a vein localizing depression mark thereupon. The depression mark thus guides the health care worker to properly insert the insertion needle into the underlying vein.

Accordingly, although the invention has been described by reference to certain preferred embodiments, it is not intended that the novel disclosures herein presented be limited thereby, but that modifications thereof are intended to be included as falling within the broad scope and spirit of the foregoing disclosure, the following claims and the appended drawings.

I claim:

1. A central venous catheter kit, the central venous catheter kit for helping a health care worker quickly and controllably gain ultrasound-supported, vascular access, said central venous catheter kit comprising:

scanning gel, the gel being superficially applicable to a skin layer for coupling the skin layer and an ultrasound device;

an insertion needle, the insertion needle for accessing a vein;

a guide wire, the guide wire being cooperable with the insertion needle for guiding structure to the accessed vein;

a wire gripping pad, the wire gripping pad for enhancing a health care worker's grip on the guide wire, the wire gripping pad being constructed from a first resiliently deformable material and comprising a first pad surface, a second pad surface opposite the first pad surface, and a central fold section, the pad being foldable at the central fold section for sandwiching the guide wire with the first pad surface, the second pad surface comprising digit-receiving notches for enhancing the health care worker' grip on the wire gripping pad, the wire gripping pad comprising a first half, a second half, and opposed lateral edges, a single digit-receiving notch being formed in the first half at the second pad surface intermediate the lateral edges for receiving the health care worker's thumb, a pair of digit-receiving notches being formed in the second half at the second pad surface in staggered relation relative to the single digit receiving notch intermediate the lateral edges for receiving at least two of the health care worker's fingers, each notch comprising a notch axis, the notch axes being parallel to the lateral edges;

a catheter, the catheter being insertable into the accessed vein via the guide wire, the guide wire being displaceable relative to the wire gripping pad via the first pad surface, the first .resiliently deformable material for enabling the health care worker to selectively and manually pinch-grip the guide wire for locating the guide wire relative to the vein;

the kit comprising a needle localizing stylus, the needle localizing stylus being constructed from a second resiliently deformable material and comprising an upper finger-engaging portion, a lower pointed portion, a circular transverse cross section, a pointed longitudinal cross section, and a tunnel, the circular transvers cross section having a center and the pointed longitudinal cross section having a tip, the tip comprising a pointed outer tip diameter, the pointed outer tip diameter for marking the skin surface in superficial adjacency to a catheterization vein, the tunnel axially extending through the needle-localizing stylus along the center to the tip, the second resiliently flexible material for enabling the health care worker to selectively an manually pinch-grip the tunnel received structure for locating said structure relative to the catheterization vein.

2. The central venous catheter kit of claim 1 wherein the needle-localizing stylus comprises an outer stylus surface, the outer stylus surface at the upper finger-engaging portion comprising stylus gripping means for enhancing a user's grip on the needle-localizing stylus.

3. The central venous catheter kit of claim 1 wherein the first pad surface comprises friction enhancing means for enhancing friction between the pad and the guide wire when the health care worker selectively and manually pinch-grips the guide wire.

4. The central venous catheter kit of claim 3 comprising digit retaining means, the digit retaining means for retaining received digits within the notches for enhancing line gripping effectiveness.

5. The central venous catheter kit of claim 4 wherein the notches comprise textured surfacing, the textured surfacing extending laterally within the notches for enhancing friction between the wire gripping pad and the health care worker's digits.

6. A central venous catheter kit, the central venous catheter kit for helping a user quickly and controllably gain vascular access, said central venous catheter kit comprising:

an insertion needle, the insertion needle for accessing a vein;

a guide line, the guide line being cooperable with the insertion needle for guiding structure to the accessed vein;

a line gripping pad, the line gripping pad for enhancing a user's manual grip on the guide line, the line gripping pad being constructed from a resiliently flexible material and comprising a first pad surface, a second pad surface opposite the first pad surface, and a central fold section, the pad being foldable at the central fold section for sandwiching the guide line with the first pad surface, the second pad surface comprising digit-receiving notches for enhancing the health care worker's grip on the line gripping pad, the line gripping pad comprising a first half, a second half, and opposed lateral edges, a single digit receiving notch being formed in the first half at the second pad surface intermediate the lateral edges for receiving the health care worker's thumb, a pair of digit-receiving notches being formed in the second half at the second pad surface intermediate the lateral edges for receiving at least two of the health care worker's fingers, each notch comprising a notch axis, the notch axes being parallel to the lateral edge;

a catheter, the catheter being insertable into the accessed vein via the guide line, the guide line being displaceable relative to the line gripping pad via the first pad surface, the resiliently flexible material for enabling the health care worker to selectively and manually pinch-grip the line guide for locating the line guide relative to the vein; and the kit comprising a needle localizing stylus, the needle localizing stylus being constructed from a second resiliently deformable material and comprising an upper finger-engaging portion, a lower pointed portion, a circular transverse cross section, a pointed longitudinal cross section, and a tunnel, the circular transverse cross section having a center and the pointed longitudinal cross section having a tip, the tip comprising a pointed outer tip diameter, the pointed outer tip diameter for marking the skin surface in superficial adjacency to a catheterization vein, the tunnel axially extending through the needle-localizing stylus along the center to the tip, the second resiliently flexible material for enabling the health care worker to selectively and manually pinch-grip tunnel-received structure for locating said structure relative to the catheterization vein.

7. The central venous catheter kit of claim 6 comprising scanning gel, the scanning gel being superficially applicable to a skin layer for coupling the skin layer and an ultrasound device for supporting vascular access.

8. The central venous catheter kit of claim 6 wherein the needle localizing stylus comprises an outer stylus surface, the outer stylus surface at the upper finger-engaging portion comprising stylus gripping means for enhancing a user's grip on the needle-localizing stylus.

9. The central venous catheter kit of claim 6 wherein the first pad surface comprises friction enhancing means for enhancing friction between the pad and the guide line when the user selectively and manually pinch-grips the guide line.

10. The central venous catheter kit of claim 6 comprising digit retaining means, the digit retaining means for retaining received digits within the notches for enhancing line gripping effectiveness.

11. The central venous catheter kit of claim 6 wherein the notches comprise textured surfacing, the textured sufacing extending laterally within the notches for enhancing friction between the pad and the user's digits.

* * * * *